(12) United States Patent
Wei et al.

(10) Patent No.: US 9,775,862 B2
(45) Date of Patent: Oct. 3, 2017

(54) MODIFICATION OF REACTIVITY OF BONE CONSTRUCTS

(75) Inventors: Guobao Wei, Milltown, NJ (US); Susan J. Drapeau, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 130 days.

(21) Appl. No.: 13/361,339

(22) Filed: Jan. 30, 2012

(65) Prior Publication Data

US 2013/0195805 A1   Aug. 1, 2013

(51) Int. Cl.

| | |
|---|---|
| *A61K 35/28* | (2015.01) |
| *A61K 38/46* | (2006.01) |
| *A61P 19/00* | (2006.01) |
| *A61K 35/12* | (2015.01) |
| *A61K 35/32* | (2015.01) |
| *A61L 27/36* | (2006.01) |
| *A61L 27/38* | (2006.01) |
| *A61L 27/50* | (2006.01) |

(52) U.S. Cl.
CPC .............. *A61K 35/28* (2013.01); *A61K 35/32* (2013.01); *A61L 27/3608* (2013.01); *A61L 27/3683* (2013.01); *A61L 27/3821* (2013.01); *A61L 27/3834* (2013.01); *A61L 27/50* (2013.01); *A61L 2300/414* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 5,073,373 | A | * | 12/1991 | O'Leary et al. .............. 424/422 |
| 5,607,269 | A | | 3/1997 | Dowd et al. |
| 6,030,635 | A | | 2/2000 | Gertzman et al. |
| 6,294,187 | B1 | | 9/2001 | Boyce et al. |
| 6,326,018 | B1 | | 12/2001 | Gertzman et al. |
| 6,338,810 | B1 | * | 1/2002 | Carpena et al. ................ 264/16 |
| 6,440,444 | B2 | | 8/2002 | Boyce et al. |

(Continued)

OTHER PUBLICATIONS

Choi, Sung-Wook; Kim, Jung-Hyun; "Design of surface-modified poly(D,L-lactide-co-glycolide) nanoparticles for targeted drug delivery to bone" Journal of Controlled Release, 122, 24-30, 2007.*

(Continued)

*Primary Examiner* — David Berke-Schlessel

(57) ABSTRACT

A method of enhancing the binding of growth factors and cell cultures to a demineralized allograft bone material which includes applying ex vivo an effective quantity of an ionic force change agent to at least a portion of the surface of a demineralized allograft bone material to produce a binding-sensitized demineralized allograft bone material and implanting the binding-sensitized demineralized allograft bone material into a host bone. The ionic force change agent may include at least one of enzymes, pressure, chemicals, heat, sheer force, oxygen plasma, supercritical nitrogen, supercritical carbon, supercritical water or a combination thereof. A molecule, a cell culture, or a combination thereof is administered to the binding-sensitized demineralized allograft bone material.

9 Claims, 1 Drawing Sheet

(56) References Cited

U.S. PATENT DOCUMENTS

| | | | |
|---|---|---|---|
| 6,451,335 B1 * | 9/2002 | Goldenheim | A61K 9/1647 424/426 |
| 6,478,825 B1 | 11/2002 | Winterbottom et al. | |
| 6,696,073 B2 | 2/2004 | Boyce et al. | |
| 6,846,853 B2 * | 1/2005 | Shimp | 523/113 |
| 7,749,555 B2 * | 7/2010 | Zanella et al. | 427/2.26 |
| 2005/0251267 A1 | 11/2005 | Winterbottom et al. | |
| 2005/0283255 A1 | 12/2005 | Geremakis et al. | |
| 2007/0098756 A1 | 5/2007 | Behnam | |
| 2007/0110820 A1 | 5/2007 | Behnam | |
| 2007/0191963 A1 | 8/2007 | Winterbottom et al. | |
| 2009/0130173 A1 | 5/2009 | Behnam et al. | |
| 2009/0192474 A1 | 7/2009 | Wei et al. | |
| 2009/0220605 A1 | 9/2009 | Wei et al. | |
| 2009/0234277 A1 | 9/2009 | Wei et al. | |
| 2010/0203155 A1 | 8/2010 | Wei et al. | |
| 2011/0054408 A1 | 3/2011 | Wei et al. | |

OTHER PUBLICATIONS

Castro-Magana, Mariano; et al; "Effect of prolonged clonidine administration on growth hormone concentrations and rate of linear growth in children with constitutional growth delay" The Journal of Pediatrics, 109, 784-787, 1986.*

* cited by examiner

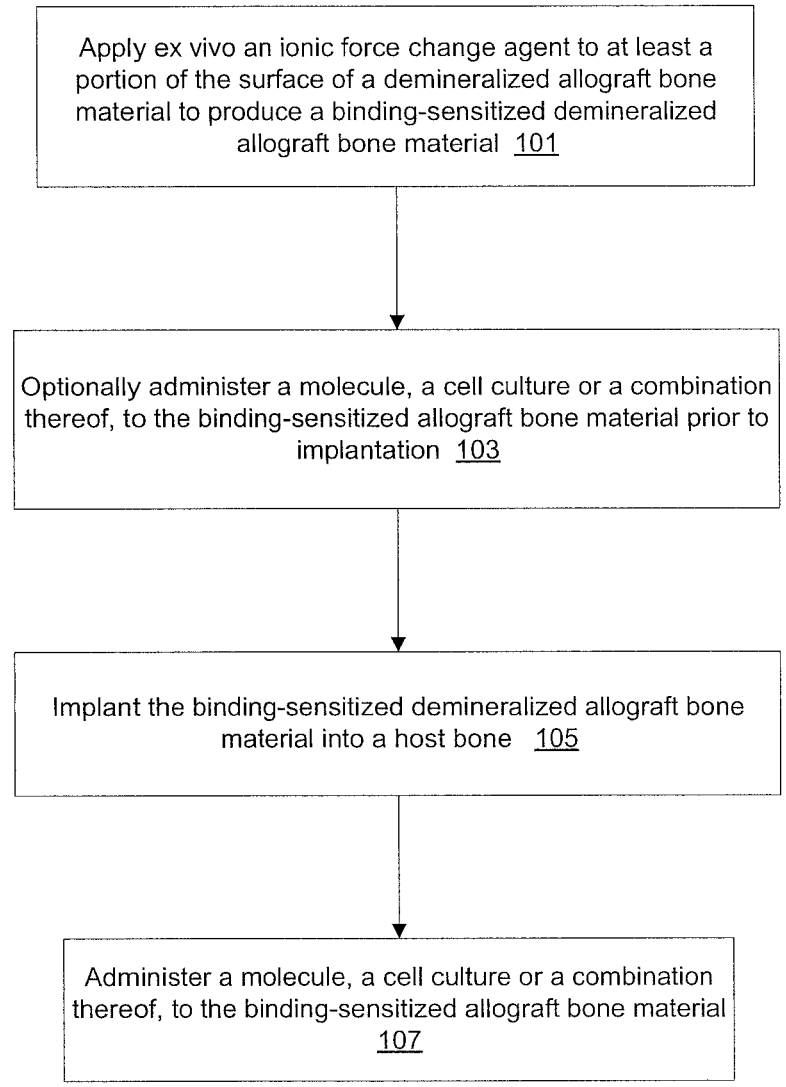

MODIFICATION OF REACTIVITY OF BONE CONSTRUCTS

BACKGROUND

Numerous approaches are being employed to improve the bone generation and repair cycle (also referred to as the bone repair cascade). Such issues are paramount in the treatment of all bone related defects related to degeneration, injury, infection, malignancy or developmental malformation. For example, in the spinal surgery field, there are several different types of autologous bone graft substitutes that are either currently available or are in various stages of development for use in spine fusion surgery.

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible. Generally, the formed implant, whether monolithic or particulated and in a carrier, is substantially solid at the time of implantation and thus does not conform to the implant site. Further, the implant is substantially complete at the time of implantation and thus provides little ability for customization, for example by the addition of autograft.

The use of bone grafts is generally limited by the available shape and size of grafts. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone.

Demineralized bone matrix (DBM) is demineralized allograft bone with osteoinductive activity. DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present. DBM includes demineralized pieces of cortical bone to expose the osteoinductive proteins contained in the matrix. These activated demineralized bone particles are usually added to a substrate or carrier (e.g. glycerol or a polymer). DBM is mostly an osteoinductive product, but lacks enough induction to be used on its own in challenging healing environments such as posterolateral spine fusion.

Allograft bone is a reasonable graft substitute for autologous bone. It is readily available from cadavers and avoids the surgical complications and patient morbidity associated with harvesting autologous bone. Allograft bone is essentially a load-bearing matrix comprising cross-linked collagen, hydroxyapatite, and osteoinductive bone morphogenetic proteins. Human allograft tissue is widely used in orthopaedic surgery.

Even though allograft tissue has certain advantages over the other treatments, one of the main drawbacks of the allograft treatment is that the ingrowth of the host bone into the grafted bone may take longer than in an autograft. As a result, allograft treatment may be less effective than the autograft. Attempts have been made to overcome these drawbacks by modifying the bone graft's surface.

Despite the advances recently made in the art, new methods promoting ingrowth of the host bone into the grafted bone are needed to better utilize the advantages of allograft treatment.

SUMMARY

The present disclosure fills the foregoing need by providing devices (e.g., medical devices), systems and methods for enhancing ingrowth of host bone. In particular, the present disclosure provides an advantageous allograft bone composition comprising modifying demineralized allograft bone to provide an ionic gradient to produce a modified demineralized allograft bone material, and implanting the modified demineralized allograft bone material. This aspect of the present disclosure may further provide administering to the modified demineralized allograft bone material a molecule, a cell culture or a combination thereof.

According to one aspect, a method for enhancing ingrowth of host bone is provided comprising the steps of modifying at least a portion of a demineralized allograft bone material to provide an ionic gradient to produce a modified demineralized allograft bone material; and implanting the modified demineralized allograft bone material.

According to another aspect, a method of enhancing the binding of growth factors and cell cultures to a demineralized allograft bone material is provided comprising the steps of: applying ex vivo an effective quantity of an ionic force change agent to at least a portion of the surface of a demineralized allograft bone material to produce a binding-sensitized demineralized allograft bone material; implanting said binding-sensitized demineralized allograft bone material into a host bone; and administering to said, binding-sensitized demineralized allograft bone material a molecule, a cell culture, or a combination thereof.

According to yet another aspect, a bone graft material is provided comprising: a biocompatible material comprising a demineralized allograft bone material, wherein at least a portion of a demineralized allograft bone material is modified to provide an ionic gradient to produce a binding-sensitized demineralized allograft bone material.

While multiple embodiments are disclosed, still other embodiments of the present disclosure will become apparent to those skilled in the art from the following detailed description, which is to be read in connection with the accompanying drawing(s). As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWING

In part, other aspects, features, benefits and advantages of the embodiments will be apparent with regard to the following description, appended claims and accompanying drawing(s) where:

FIG. 1 is an exemplary block diagram of a method for enhancing the binding of growth factors and cell cultures to a demineralized allograft bone material.

DEFINITIONS

To aid in the understanding of the disclosure, the following non-limiting definitions are provided:

"Bioactive agent or bioactive compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

"Biocompatible," as used herein, refers to materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the disclosure. In some embodiments, demineralized bone has less than 95% of its original mineral content. Demineralized is intended to encompass such expressions as "substantially demineralized," "partially demineralized," and "fully demineralized."

"Demineralized bone matrix," as used herein, refers to any material generated by removing mineral material from bone tissue. In some embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the disclosure.

"Osteoconductive," as used herein, refers to the ability of a non-osteoinductive substance to serve as a suitable template or substance along which bone may grow.

"Osteogenic," as used herein, refers to the ability of an agent, material, or implant to enhance or accelerate the growth of new bone tissue by one or more mechanisms such as osteogenesis, osteoconduction, and/or osteoinduction.

"Osteoimplant," as used herein, refers to any bone-derived implant prepared in accordance with the embodiments of this disclosure and therefore is intended to include expressions such as bone membrane, bone graft, etc.

"Osteoinductive," as used herein, refers to the quality of being able to recruit cells from the host that have the potential to stimulate new bone formation. Any material that can induce the formation of ectopic bone in the soft tissue of an animal is considered osteoinductive.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "morbidity" refers to the frequency of the appearance of complications following a surgical procedure or other treatment.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols, which have only a marginal effect on the patient.

The term "xenograft" refers to tissue or organs from an individual of one species transplanted into or grafted onto an organism of another species, genus, or family.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Aspects of the present disclosure provide reagents, methods and systems for enhancing ingrowth of host bone. Applicants have found that modifying a demineralized allograft bone material to provide an ionic gradient to produce a modified demineralized allograft bone material, and implanting the modified demineralized allograft bone material results in enhanced ingrowth of host bone.

In one embodiment of the present disclosure an ionic force change agent is applied to modify the demineralized allograft bone material. According to one embodiment of the disclosure, the demineralized allograft bone material may comprise a demineralized bone matrix (DBM) comprising fibers, particles and any combination of thereof. According to another embodiment, a bone graft structure may be used which comprises a composite bone which includes a bone powder, a polymer and a demineralized bone.

The ionic force change agent may be a binding agent, which modifies the demineralized allograft bone material or bone graft structure to bind molecules, such as, for example, growth factors, or cells, such as, for example, cultured cells, or a combination of molecules and cells. In the practice of the disclosure the growth factors include but are not limited to BMP-2, rhBMP-2, BMP-4, rhBMP-4, BMP-6, rhBMP-6, BMP-7 (OP-1), rhBMP-7, GDF-5, LIM mineralization protein, platelet derived growth factor (PDGF), transforming growth factor-β (TGF-β), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the disclosure is not limited to growth factors only. Other molecules can also be employed in the disclosure. For example, tartrate-resistant acid phosphatase, which is not a growth factor, may also be used in the disclosure.

If a cell culture is employed, the cells include but are not limited to mesenchymal stems cells, pluripotent stem cells, embryonic stem cells, osteoprogenitor cells, osteoblasts, osteoclasts, and any bone marrow-derived cell lines.

In one embodiment of the method of the disclosure, the ionic forces of the demineralized allograft bone material are changed by a one-to-one substitution of the calcium ion with an element selected from the group consisting of lithium, sodium, potassium and cesium ions of hydroxyapatite.

Another aspect of the present disclosure provides a method of enhancing the binding of molecules and cell cultures to a demineralized allograft bone material comprising applying ex vivo an effective quantity of an ionic force change agent to the demineralized allograft bone material to produce a binding-sensitized demineralized allograft bone material; and implanting said binding-sensitized demineralized allograft bone material into a host bone. It may be desirable to administer to the binding-sensitized demineralized allograft bone material a molecule, a cell culture or a combination thereof all of which are capable of binding to said binding-sensitized demineralized allograft bone material. For example, the molecule may be a growth factor such as, for example, BMP-2, rhBMP-2, BMP-4, rhBMP-4, BMP-6, rhBMP-6, BMP-7 (OP-1), rhBMP-7, GDF-5, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), and rhGDF-5. Other molecules can also be employed in the disclosure, such as, for example, tartrate-resistant acid phosphatase, which is not a growth factor.

Cells may also be used instead of or in addition to molecules, such as growth factors. Non-limiting examples of suitable cell types include mesenchymal stems cells, pluripotent stem cells, embryonic stem cells, osteoprogenitor cells, osteoblasts and osteoclasts.

Depending upon the condition of the patient, new bone ingrowth is accomplished by one or more mechanisms such as osteogenesis, osteoconduction and osteoinduction. It can be appreciated that the needs of a child are different from an aging patient afflicted with osteoporosis. Accordingly, there is no "one size fits all" approach towards optimizing the healing conditions in a patient.

In one aspect, the disclosure relates to a method of modifying a demineralized allograft bone material (also referred to as an implant) in such a way that the original chemical forces naturally present have been altered in such a way as to attract and bind growth factors, other proteins and cells affecting osteogenesis, osteoconduction and osteoinduction.

Intramolecular or intermolecular attractions between atoms are formed through weak chemical forces, which include hydrogen bonds, van der Waals forces, ionic bonds and hydrophobic interactions. These weak forces create bonds that are constantly forming and breaking at physiological temperature and are readily reversible under physiological conditions. The transient bonds between metabolites and macromolecules, and hormones and receptors, and all the other cellular moieties necessary for life are required for biomolecular interactions since rigid, static bonds will inhibit, if not paralyze, cellular activities.

In one aspect of the disclosure, the implant or demineralized allograft bone material is modified in such a way that the original chemical forces naturally present are altered so that the implant attracts and binds proteins, such as, for example, growth factors and cells, including cells from cell cultures.

The disclosure provides for a method of enhancing ingrowth of host bone by modifying a bone graft material, in particular demineralized allograft bone material, to provide a gradient, implanting the modified demineralized allograft bone material, and administering to the modified demineralized allograft bone material a molecule, such as, for example, a growth factor, and/or a cell culture. A person of ordinary skill in the art will appreciate that the molecule and/or the cell culture may be administered to the modified demineralized allograft bone material before and/or after implanting the modified demineralized allograft bone material into the host bone.

Non-limiting examples of a bone graft material include demineralized bone matrix, or a bone composite.

According to some embodiments of the disclosure, the demineralized bone matrix may comprise demineralized bone matrix fibers and/or demineralized bone matrix chips. In some embodiments, the demineralized bone matrix may comprise demineralized bone matrix fibers and demineralized bone matrix chips in a 30:60 ratio.

According to one embodiment of the disclosure, the bone composite comprises a bone powder, a polymer and a demineralized bone. In different embodiments of the disclosure, bone powder content can range from about 5% to about 90% w/w, polymer content can range from about 5% to about 90% w/w, and demineralized bone particles content comprises the reminder of the composition. Preferably, the demineralized bone particles comprise from about 20% to about 40% w/w while the polymer and the bone powder comprise each from about 20% to about 60% w/w of the composition. The bone graft materials of the present disclosure include those structures that have been modified in such a way that the original chemical forces naturally present have been altered to attract and bind molecules, including, without limitation, growth factors and/or cells, including cultured cells.

The disclosure also discloses a method of enhancing binding of molecules, such as, for example, growth factors and cell cultures by applying ex vivo an effective quantity of an ionic force change agent to a demineralized allograft bone material, in particular, the surface of a demineralized allograft bone material, to produce a binding-sensitized demineralized allograft bone material, and implanting the binding-sensitized demineralized allograft bone material. An effective amount of molecules, including growth factors and cell cultures can be administered to the binding-sensitized demineralized allograft bone material both before and after implanting the modified demineralized allograft bone material into the host bone.

In another aspect, the disclosure involves the addition of an ionic force change agent to the demineralized allograft bone material thereby modifying its surface, namely modifying its charge in a targeted manner to produce an appropriately charged demineralized allograft bone material. The ionic force change agent may be applied to the entire demineralized allograft bone material or to selected portions/surfaces thereof.

In some embodiments, the ionic force change agent comprises at least one of enzymes, enzyme mixtures, pressure (e.g., isostatic pressure), chemicals, heat, sheer force, oxygen plasma, or a combination thereof. For example, the ionic force change agent may comprise an enzyme such as collagenase or pepsin, which can be administered for a sufficient period of time to partially digest at least a portion of the demineralized allograft bone material. Subsequently, the enzyme may be deactivated and/or removed.

Any enzyme or enzyme mixture may be contemplated, and treatment time durations may be altered in accordance with the enzyme(s) used. Some suitable enzymes that may degrade the DBM material include, but are not limited to, cysteine proteinases, matrix metalloproteinases, enzymes such as amylases, proteases, lipases, pectinases, cellulases, hemicellulases, pentosanases, xylanases, phytases or combinations thereof. Exemplary enzymes suitable to partially degrade and modify the DBM material, include but are not limited to, cathepsin L, cathepsin K, cathepsin B, pepsin, plasminogen, elastase, stromelysin, plasminogen activators, matrix metalloproteinases (MMPs), including but not limited to collagenase and gelatinase, or a combination thereof. In some embodiments, the DBM material can be subjected to pressure to modify it. The simplest pressing technique is to apply pressure to the unconstrained DBM material. Examples include pressing the DBM material using a mortar and pestle, applying a rolling/pressing motion such as is generated by a rolling pin, or pressing the bone pieces between flat or curved plates. These flattening pressures cause the DBM material fibers to remain intact.

Another pressing technique involves mechanically pressing demineralized bone material, which can be constrained within a sealed chamber having a hole (or a small number of holes) in its floor or bottom plate. The separated fibers extrude through the holes with the hole diameter limiting the maximum diameter of the extruded fibers. This constrained technique results in fibers that are largely intact (as far as length is concerned).

In a combined unconstrained/constrained pressing technique that results in longer fibers by minimizing fiber breakage, the demineralized bone is first pressed into an initially separated mass of fibers while in the unconstrained condition and thereafter these fibers are constrained within the sealed chamber where pressing is continued.

In general, pressing of demineralized bone to provide demineralized bone particles can be carried out at from about 1,000 to about 40,000 psi, and preferably at from about 5,000 to about 20,000 psi.

Subsequent to the addition of the ionic force change agent, the practitioner may optionally administer an appropriate molecule or cell culture. Generally, the molecule or cell culture is applied within minutes, for example from about 1 to about 120 minutes before implantation into the patient.

One class of molecules suitable for one embodiment of the disclosure is growth factors. Growth factors suitable for use in the practice of the disclosure include but are not limited to bone morphogenic proteins, for example, BMP-2, rhBMP-2, BMP-4, rhBMP-4, BMP-6, rhBMP-6, BMP-7 (OP-1), rhBMP-7, GDF-5, and rhGDF-5. Bone morphogenic proteins have been shown to be excellent at growing bone and there are several products being tested. For example, rhBMP-2 delivered on an absorbable collagen sponge (INFUSE® Bone Graft, Medtronic Sofamor Danek, Memphis, Tenn.) has been used inside titanium fusion cages and resulted in successful fusion and can be used on a ceramic carrier to enhance bone growth in a posterolateral fusion procedure. rhBMP-2 can also be used on a carrier for acute, open fractures of the tibial shaft. BMP-7 (OP-1) also enhances bone growth in a posterolateral fusion procedure.

Additionally, suitable growth factors include, without limitation, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), and beta-2-microglobulin (BDGF II).

Further, molecules, which do not have growth factor properties may also be suitable for this disclosure. An example of such molecules is tartrate-resistant acid phosphatase.

In one embodiment, the demineralized allograft bone material is treated with a negatively-charged ionic force change agent to produce a negatively-charged demineralized allograft bone material. The negatively-charged demineralized allograft bone material attracts a positively charged molecule having a pI from about 8 to about 10. Examples of positively charged molecules having a pI from about 8 to about 10 include but are not limited to, rhBMP-2 and rhBMP-6.

In another embodiment, the demineralized allograft bone material is treated with a positively-charged ionic force change agent such that the positively-charged demineralized allograft bone material attracts a molecule with a slightly negative charge, for example a charge of pI about 5 to about 7. Examples of molecules having a slightly negative charge include rhBMP-4.

In yet another embodiment, the demineralized allograft bone material is treated with a positively-charged ionic force change agent to produce a positively-charged demineralized allograft bone material such that cells, in particular cell cultures having a negative surface charge bind to the positively-charged demineralized allograft bone material. Examples of cells which are suitable for use in the practice of the disclosure include but are not limited to mesenchymal stems cells, pluripotent stem cells, embryonic stem cells, osteoprogenitor cells and osteoblasts.

The mechanisms by which a demineralized allograft bone material may acquire ionic forces include but are not limited to ionization, ion adsorption and ion dissolution.

In one embodiment, the implant is modified to give it the selected charge by a one-to-one substitution of the calcium ion with lithium, sodium, potassium or cesium of hydroxyapatite.

In yet another aspect, treatments with gradient-affecting elements, such as elements present in hydroxyapatite, and human proteins are employed. Suitable gradient-affecting proteins are those present in the organic phase of human bone tissue. The gradient-affecting proteins derive molecule or cell attraction without the potential damaging effects on the implants, as may be the case with other chemical treatments. Usually this is accomplished through surface treatments such as, for example, plasma treatment to apply an electrostatic charge on bone.

The term "plasma" in this context is an ionized gas containing excited species such as ions, radicals, electrons and photons. The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces. Plasma treatment is an effective method to uniformly alter the surface properties of substrates having different or unique size, shape and geometry including but not limited to bone and bone composite materials.

FIG. 1 is an exemplary block diagram of a method for enhancing the binding of growth factors and cell cultures to a demineralized allograft bone material. In step 101, an ionic force change agent is applied ex vivo to at least a portion of a surface of a demineralized allograft bone material (e.g., demineralized bone matrix (DBM) material fibers or DBM material particles) to produce a binding-sensitized demineralized allograft bone material. In some embodiments, the ionic force change agent may comprise at least one of enzymes, pressure (e.g., isostatic pressure), chemicals, heat, sheer force or plasma to alter and/or charge the surface, to render the demineralized bone matrix material more reactive, chemically and/or physically.

For example, such surface treatment or modification of demineralized bone matrix material advantageously exposes functional groups so as to increase reactivity and bonding with other molecules. In particular, this would enhance reactivity of the demineralized bone matrix material so that it can better immobilize or bind with drugs, proteins, or other molecules when, e.g., implanted in vivo.

In some embodiments, the ionic force change agent may comprise an enzyme, such as, e.g., collagenase or pepsin. Usage of alternative enzymes may be contemplated. The demineralized bone matrix material may be treated with an enzyme or enzyme mixture for a period of time, e.g., sufficient to cause at least a portion of the demineralized bone matrix material to become at least partially digested. Subsequently, the enzyme/enzyme mixture may be deactivated. This enzyme treatment will cause the demineralized bone matrix material to become "sticky" and thus cause physical entanglement of the demineralized bone matrix particles/fibers and/or improve reactivity of the demineralized bone matrix particles/fibers with other molecules.

In optional step 103, a molecule, a cell culture or any combination thereof, may be administered to the binding-sensitized allograft bone material prior to implantation. For example, drugs, proteins or other molecules which are desired to be bound to the DBM material may be administered to the binding-sensitized demineralized allograft bone material.

In step 105, the binding-sensitized demineralized allograft bone material (with or without additional molecules and/or cell cultures bound thereto) may be implanted into a host bone. In step 107, a molecule, a cell culture or any combination thereof, may be administered to the binding-sensitized allograft bone material after implantation.

A modified demineralized allograft bone material may be used in conjunction with a delivery system for delivering the modified demineralized allograft bone material to a surgical site. The delivery system may comprise a covering wherein the modified demineralized allograft bone material is provided within the covering for delivery to the surgical site. Generally, the covering may be a single or multi-compartment structure capable of at least partially retaining the modified demineralized allograft bone material provided therein until the covering is placed at a surgical site. Upon placement, the covering facilitates transfer of the modified demineralized allograft bone material surrounding the surgical site. The covering may participate in, control, or otherwise adjust, the release of the substance or penetration of the covering by surrounding materials, such as cells or tissues.

A covering according to some embodiments may comprise natural and synthetic polymers which provide and extended and/or increased shelf life to the delivery system. The extended shelf life of the polymers prevents environmental degradation of the covering, thus increasing efficiency, preventing waste and providing a more effective, usable product over an extended period of time.

In some embodiments, the covering may be used for containment of particulate or morselized materials (the substance provided in the covering), optionally to provide a focus or concentration of biological activity. In some embodiments, the covering may be used for maintaining materials (the substance provided in the covering) in spatial proximity to one another, possibly to provide a synergistic effect. In some embodiments, the delivery system may be used to control availability of substances provided within the delivery system to cells and tissues of a surgical site over time. In some embodiments, the delivery system may be used for delivery through a limited opening, such as in minimally invasive surgery or mini-open access. In some embodiments, the delivery system may be used to deliver morselized or particulated materials (the substance provided in the covering) in pre-measured amounts. In other embodiments, the substance may be liquid or flowable, or combinations of these with particulate, morselized, and/or other materials.

In various embodiments, the covering can contain a demineralized allograft material. The covering limits, and in some embodiments eliminates graft migration and maintains graft density. The delivery system, with contained demineralized allograft material, may be configured to conform to surrounding bony contours or implant space. In some embodiments, the delivery system provides a pathway for healing/cell penetration and tissue ingrowth. Thus, the covering may facilitate transfer of a substance out of the covering or transfer or surrounding materials at the surgical site, such as cells and tissues, into the covering.

The covering may have a single compartment or may have a plurality of compartments. Thus, in one embodiment, the covering is dual-compartment and comprises first and second compartments. A first substance may be provided in the first compartment and a second substance may be provided in the second compartment. The second compartment may be adjacent to, apart from, inside, or surrounding the first compartment. Materials forming the first compartment and the second compartment may be the same or different. Selection of materials, positioning of the compartments, and other factors relating to the first and second compartments may be chosen to achieve simultaneous or sequential delivery or release of a substance or substances.

Covering Material

The covering may comprise a structural material and, in some embodiments, a functional material. The structural material may comprise a mesh material, a polymeric material, or other. The functional material may comprise, for example, a radiopaque material, a bacteriocidal material, or other material.

In various embodiments, in accordance with the specific application for which the covering is being used, the covering may be rigid, may be flexible, may be non-elastic, or may be elastic. The covering material may be braided, woven, non-woven shape memory, particulate, threaded, porous, or non-porous.

The covering may participate in, control, or otherwise adjust the release of the substance. For example, the covering may act as a selectively permeable membrane and/or may be porous, with the level of porosity being related to the nature of the substances inside the covering. Thus, the material for and configuration of the covering may be selected or adjusted based on desired release characteristics. Specific properties that may be adjusted include thickness, permeability, porosity, strength, flexibility, elasticity, and others of the covering material. It is to be appreciated that some of these properties may depend on others. For example, the thickness and porosity of the material may contribute to its strength, flexibility, and elasticity.

In some embodiments, the covering may be porous to fluid and/or cells, may be biocompatible, and may be resistant to rupture (including should the substance provided therein swell). In some embodiments, the covering with the demineralized allograft material provided therein may be loadbearing. The covering may be resorbable or non-resorbable. The covering may provide increased handling properties, may have irrigation resistance, and/or may support cellular penetration. Flexibility of the covering may be selected to suit particular applications. In some applications, it may be desirable to have a flexible covering.

If the covering is made from a resorbable material, the covering degrades and disappears after a period of time. If the covering is not made of a resorbable material, the covering remains in the body. Tissue ingrowth may occur to bind the host tissue to the substance provided within the covering. Tissue ingrowth through and around the covering, between the host tissue and the substance provided within the covering, may be promoted via openings in the covering.

In various embodiments, the covering may comprise a porous material or a mesh material. The size of the pores of the covering may be designed to permit cellular infiltration (approximately several microns to several millimeters), but may also be designed specifically to exclude cells for the inside of the covering (e.g. approximately 0.45 microns) and only allow diffusion of small molecules (proteins and hormones). Thus, the covering may act to control access to the interior of the delivery system by cells. In embodiments comprising more than one compartment, characteristics of the covering material may be varied between compartments. Generally, the porosity, flexibility, strength, or any other characteristic of one compartment may vary from that characteristic of the other compartment.

The covering may be formed of a resorbable or nonresorbable, natural or synthetic biocompatible material. In some embodiments, more than one material may be used, including as multiple layers. For example, in an embodiment comprising two compartments, one or more materials may be used for the first compartment and a different material or materials may be used for the second compartment. For example, one compartment or portions thereof may be made of material or materials that provide a desired property or properties relative to other compartments or portions thereof, such as increased or decreased resorbability or stiffness, or the different compartments or portions thereof may be imparted with different drug delivery properties, etc. Alternatively, all compartments may comprise the same material or mixtures of materials. Where the characteristics of the material are varied between compartments, or over the surface of a single compartment, the pores of the first compartment or portion thereof may be larger than the pores of the second compartment.

The covering may comprise any suitable structure for delivering a substance in vivo. Thus, as described, the covering may comprise a mesh. In other embodiments, the covering may comprise a polymeric structure with a chamber provided therein. The chamber may be filled with a substance for delivering in vivo, such as demineralized allograft material, fully mineralized bone material, or others disclosed herein.

In some embodiments, the covering may expand when placed in the body. Expansion can be provided in at least two ways: the covering may be compressed such that the covering expands when placed in the body or the covering may be made of a material that expands when it comes in contact with water or other bodily fluids, either by way of liquid absorption, or by stretching when the materials inside it absorb liquid and themselves expand. In some embodiments, the covering may comprise a shape memory material such as copper-zinc-aluminum-nickel alloy, copper-aluminum-nickel alloy, and nickel-titanium (NiTi) alloy. Reinforcing materials such as cortical bone, calcium phosphates, etc. may be incorporated into the structure of the covering to reinforce it.

The covering may be configured for specific compressive strength and rigidity by adjusting density and resorption time of the covering. In some embodiments, a coating may be provided over the covering. For example, the coating may be a compound of poly-L-lactide, of polyglycolic acid, or their polymers. The coating may be selected such that it has a resorption time wherein it is resorbed by the body and the material within the covering is permitted to exit through openings in the covering.

Exemplary Covering Materials

A covering according to an aspect of the present disclosure, the covering may comprise demineralized allograft material and at least one of bioerodible polymers, bioabsorbable polymers, biodegradable biopolymers, synthetic polymers, copolymers and copolymer blends and combinations thereof. Exemplary materials may include biopolymers and synthetic polymers such as human skin, human hair, bone sheets, collagen, fat, thin cross-linked sheets containing fibers and/or fibers and chips, degradable sheets made from polyethylene glycol (PEG), chitosan sheets, alginate sheets, cellulose sheets, hyaluronic acid sheet, as well as copolymer blends of poly (lactide-co-glycolide) PLGA.

Exemplary materials may include polymeric material, woven material and braided material, non-woven; shape memory material; using outer particles to contain inner particles; attach particles to threads; add porosity to mesh fibers; non-porous materials; non-porous materials. In some embodiments, materials may be used for portions of the covering, such as for a compartment of the covering, that are substantially impenetrable.

In some embodiments, the covering may comprise a mesh material. Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, and others. Other suitable materials include carbon fiber, metal fiber, and various meshes. In other embodiments, the covering may comprise non-woven material such as spun cocoon or shape memory materials having a coil shape or shape memory alloys.

Generally, the covering may be formed of any natural or synthetic structure (tissue, protein, carbohydrate) that can be used to form a covering configuration. Thus, the covering may be formed of a polymer (such as polyalkylenes (e.g., polyethylenes, polypropylenes, etc.), polyamides, polyesters, poly(glaxanone), poly(orthoesters), poly(pyrolicacid), poly(phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite, etc.), PEEK (polyether-etherketone), dessicated biodegradable material, metal, composite materials, a biocompatible textile (e.g., cotton, silk, linen), extracellular matrix components, tissues, or composites of synthetic and natural materials, or other. Various collagen materials can be used, alone or in combination with other materials, including collagen sutures and threads. Any suitable collagen material may be used, including known collagen materials. Some examples include polymer or collagen threads woven, or knitted into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds; etc.

In some embodiments, mesh fibers may be treated to impart porosity to the demineralized allograft material that is in fiber form. This may be done, for example, to PLA, PLGA, PGA, and other fibers. One suitable method for treating the mesh fibers comprises supercritical carbon dioxide, supercritical nitrogen, or supercritical water treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated such as by having particles adhered thereto. The particles may be, for example, bone particles, demineralized allograft material, or the like. Thus, in one embodiment, the covering may comprise a plurality of threads formed into a fabric. The threads may have particles adhered thereto. For example, the threads may have particles strung on the thread. In an alternative embodiment, the covering may be formed of a material and the material may be coated with particles.

In yet other embodiments, the covering may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery system for delayed delivery of cells, growth factors, or bone morphogenetic proteins is provided comprising a nonporous covering.

In particular, in various embodiments, the device may comprise a bioerodible, a bioabsorbable, and/or a biodegradable biopolymer that may provide immediate release, or sustained release of the clonidine. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG and/or PEG may be used as a plasticizer for PLGA, but other polymers/excipients may be used to achieve the same effect. mPEG imparts malleability to the resulting formulations. In some embodiments, these biopolymers may also be coated on a medical device to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the medical device. In some embodiments, the range of the coating on the medical device ranges from about 5 microns to about 250 microns or 5 microns to about 200 microns to delay release from the medical device.

In various embodiments, the medical device comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

Functional Material Characteristics

The covering material may have functional characteristics. Alternatively, other materials having functional characteristics may be incorporated into the covering. Functional characteristics may include radiopacity, bacteriocidity, source for released materials, tackiness, etc. Such characteristics may be imparted substantially throughout the covering or at only certain positions or portions of the covering.

Suitable radiopaque materials include, for example, ceramics, mineralized bone, ceramics/calcium phosphates/calcium sulfates, metal particles, fibers, and iodinated polymer. Polymeric materials may be used to form the covering and be made radiopaque by iodinating them. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

Functional material, such as radiopaque markers, may be provided at one or more locations on the covering or may be provided substantially throughout the covering. Thus, for example, in a tubular covering, a radiopaque marker may be provided at a tip of the tubular covering. Such marker may facilitate placement of the covering. Radiopaque materials may be incorporated into the covering and/or into the substance for delivery by the covering. Further, radiopaque materials may be provided at only some locations on the covering such that visualization of those locations provides indication of the orientation of the covering in vivo.

The covering itself may be designed to release materials during degradation of the covering material. Thus, bone morphogenic proteins (BMPs), growth factors, antibiotics, angiogenesis promoting materials (discussed more fully below), bioactive agents (discussed more fully below), or other actively releasing materials may be incorporated into the covering material such that as the covering material is degraded in the body, the actively releasing material is released. For example, an actively releasing material may be incorporated into a biodegradable polymer covering such as one manufactured of a biodegradable polyester such as poly(lactic acid) (PLA), poly(glycolic acid) (PGA), poly (lactic-co-glycolic acid) (PLGA), or polyhydroxyalkanoates (polyhydroxybutyrates and polyhydroxyvalerates and copolymers). In some embodiments, poly(ethylene glycol) (PEG) may be incorporated into the biodegradable polyester to add hydrophilic and other physico-chemical properties to enhance drug delivery. In some embodiments, composites of allograft bone and biodegradable polymers (for example, PLEXUR® products available from Osteotech™) may be used in the covering.

In some embodiments, the covering may comprise a material that becomes tacky upon wetting. Such material may be, for example, a protein or gelatin based material. Tissue adhesives, including mussel adhesive proteins and cyanoacrylates, may be used to impart tackiness to the covering. In further examples, alginate or chitosan material may be used to impart tackiness to the covering. In further embodiments, an adhesive substance or material may be placed on a portion of the covering or in a particular region of the covering to anchor that portion or region of the covering in place at an implant site.

In one embodiment, the covering comprises two compartments, first and second materials may be used for the first and second compartments, respectively. The first material may release or expose a growth factor according to a first rate and the second material may release a growth factor according to a second rate. Further, the growth factors released by the first and second compartments may be the same or may be different. For example, an angiogenic growth factor may be provided with the first compartment and an osteoinductive growth factor may be provided with the second compartment in addition to the modified demineralized allograft material.

Mesh Formulation

Any suitable technique may be used for forming a material for the covering. Generally, the material may be formed as a substantially solid material, as a sheet, as a mesh, or in other configuration. In some embodiments, the material may be a textile type material. Thus, for example, the material may be formed using a textile approach such as be weaving, rug making, knitting, etc. Such formation may be by a mechanical or industrial method. In another embodiment, a substantially solid sheet may be formed and may be treated to assume a configuration penetrable by cells, fluids, and proteins. For example, the sheet may be perforated, may be expanded to create openings, or other. Also, it would be perfectly suitable to take a thin sheet of the covering material, and to perforate it, expand it to create openings, or otherwise make it penetrable by cells, fluids and proteins.

In one embodiment, elongated bone-derived particles or fragments of small intestinal submucosa may be combined longitudinally into three small bundles, each having, for example, from about 1 to about 3 tissue particles. The three bundles may then be braided. Various methods of braiding and types of braids any of which may be useful in producing the material of the disclosure herein are also described. The ends of the braided tissue-derived particles may then be glued together using a fixation agent to prevent their unraveling, or they may be held together with a biocompatible polymer or metal band.

In an alternative embodiment, the modified demineralized allograft material may be combined with a solvent to form a material. Exemplary solvents include water, lower alkanols, ketones, and ethers and mixtures of any of these or other materials. The material may then be extruded at an appropriate temperature and pressure to create a thread. Threads may also be produced by spinning, drawing, rolling, solvent-extruding, cutting or laser cutting from a sheet or bar stock. The material may alternatively be cast or molded into a solid sheet or bar stock and then cut into thin threads. These may be used immediately or woven into a mesh. Alternatively or in addition, they may be spliced, wrapped, plied, cabled, braided, woven, or some combination of these. The material may be shaped by thermal or chemical bonding, or both. In one embodiment, a portion of the solvent is removed from the material before extrusion.

Alternatively or in addition, the material may be cast as a slurry, extruded, or molded and then mixed with the modified demineralized allograft material. For example, the material may be solvent cast using a press such as a Carver press to spread the material into a film. Solvent evaporation will yield a porous film. Alternatively, the material may be compression molded into a film. The mesh size or porosity of the film will depend on the thickness of the film and the viscosity of the precursor and can be easily manipulated by one skilled in the art. Where elongated particles are used in an extruded aggregate, they will tend to be aligned roughly parallel to one another.

In an alternative embodiment, a thread of a biocompatible natural or synthetic material, for example, polylactide or collagen, may be coated with tissue-derived or other elements, for example, by dubbing. For example, a polymer fiber may be coated with an adhesive, for example, lecithin, and bone particles or other osteoconductive or osteoinductive fibrils allowed to adhere to the thread. The thread may then be twisted on itself or with a second or a plurality of similarly treated threads. Alternatively or in addition, the threads may be braided. The adhesive may be a lipid that is waxy at room temperature, for example, a di- or tri-glyceride that is solid at room temperature. Alternatively or in addition, the adhesive may be a phosphocholine or phosphatidylcholine. In some embodiments, the adhesive is a material that binds both the thread and the material that is used to coat the thread (e.g., bone particles) but that does not degrade either. Non-aqueous adhesives may improve the stability of the final aggregate as compared to aqueous adhesives.

Suitable fibers may be formed utilizing well known techniques, e.g., braiding, plying, knitting, weaving, felting, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of noncrosslinked collagen and two threads of crosslinked collagen. One skilled in the art will recognize that these techniques may be applied to the other fibrous materials described herein.

Fibers and more evenly dimensioned particles may also be plied into yarns using the same methods and same machinery known to those skilled in the art in plying threads made out of other material, e.g., cotton, polyester, etc.

Elongated materials including multistranded materials, e.g., braids, plied yarns, cables, etc., may be knitted into tubular or flat fabrics by using techniques known to those skilled in the art of producing fabrics manufactured from other types of threads. Various biologically active substances can be incorporated in, or associated with, the braided, knitted, or woven materials. Particles and fibers and materials of these (including multistranded materials) may alternatively or additionally be assembled into a material by non-woven methods such as laying, needle-punching, and hooking. For example, a thread may be attached to another thread or a pressed film.

Regardless of the assembly method, the material shape, mesh size, cable thickness, and other structural characteristics, e.g., architecture, may be customized for the desired application. For example, where a two dimensional aggregate is used to retain a thixotropic material within a gap, a tight weave is preferred to prevent leakage. To optimize cell or fluid migration through the mesh, the pore size may be optimized for the viscosity and surface tension of the fluid or the size of the cells. For example, pore sizes on the order of approximately 100-200 µm may be used if cells are to migrate through the mesh. Mesh size may be controlled by physically weaving strands of the material by controlling the ratio of solvent to solids in a precursor material.

Cells may be seeded onto the material, or contained within it. In one embodiment, cells may be encapsulated in a matrix such as alginate or collagen gel and the capsules placed on the material. Seeded materials generally do not need to be incubated for long periods of time in solutions that could partially dissolve the binding agent. Instead, the capsules may be placed on the material or covering shortly before implantation. In another embodiment, cells are simply mixed with a gel, which is then combined with the material. Alternatively, a material or covering may be cultured with cells before implantation. In one embodiment, thicker materials are used for culturing to increase mechanical integrity during implantation. Any class of cells, including connective tissue cells, organ cells, muscle cells, nerve cells, and stem cells, may be seeded onto the implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

Covering Configurations

The shape, configuration, or form of the covering may be selected for particular applications. Such shape and configuration may include, for example, the basic shape of the covering (e.g., a cylinder or a bag), whether the covering has a single or a plurality of compartments, and whether the covering includes attachment mechanisms. The covering (or delivery system) may be configured to conform to surrounding bony contours of the space in which it is placed.

As previously discussed, the covering may be formed of as a mesh. Thus, the covering may comprise a woven material. The woven material may have varying degrees of permeability. It may be permeable, semi-permeable, or non-permeable. Permeability may be with respect to cells, to liquids, to proteins, to growth factors, to bone morphogenetic proteins, or other. In further embodiments, the material may be braided.

In alternative embodiments, the covering may comprise a substantially solid structure, such as a polymer structure with a chamber, or a spun cocoon.

The covering may have any suitable configuration. For example, the covering may be formed as a ring, a cylinder, a cage, a rectangular shape, a mesh, a suture-like wrap, a continuous tube, or other configuration. In specific embodiments, the covering may be formed as a thin tube designed to be inserted through catheters or an introducer tube, a rectangular shape designed to fit adjacent to spinal processes for posterolateral spine fusion, a cube like structure designed to fit between vertebral bodies or within cages for interbody spinal fusion, a tube-like shape where the ends are designed to be fitted onto nonunion long bone defects, relatively flat shapes designed to fill cranial or maxillofacial defects, rectangular structures designed for osteochondral defects, structures preshaped to fit around various implants (e.g., dental, doughnut with hole for dental implants), or relatively elastic ring-like structures that will stretch and then conform to shapes (e.g. rubber band fitted around processes). In an embodiment wherein the covering is formed as a cage, the cage may comprise a plurality of crossed filaments, which define between them a series of openings for tissue ingrowth. Any of these shapes may be used for a covering comprising a plurality of compartments. For example, in a tubular embodiment, the tube may be formed into a plurality of compartments by tying a cord around the tube at one or more points, or by other suitable mechanism such as crimping, twisting, knotting, stapling, sewing, or other method. The configuration of the covering may be determined by the substance to be provided within the covering. For example, if the substance to be contained comprises fibers, the covering may be formed as strings or sutures that are wrapped around the fibers.

In certain embodiments, a bone void can be filled. A compartment within the covering material can be at least partially filled with a bone repair substance (e.g., demineralized allograft material). In various embodiments, at least partially filled as used herein, can mean that a percentage of the volume of a compartment (or covering material, as applicable) is at least 70% occupied, at least 75% occupied, at least 80% occupied, at least 85% occupied, at least 90% occupied, at least 95% occupied, or 100% occupied. The covering material can be inserted into an opening in the defect until the defect is substantially filled. In various embodiments, a substantially filled as used herein can mean that a percentage of the volume of a defect (or covering material, as applicable) is at least 70% occupied, at least 75% occupied, at least 80% occupied, at least 85% occupied, at least 90% occupied, at least 95% occupied, or 100% occupied. The excess material extending beyond the surface of the bone if the bone were without the defect can then be removed, or at least partially removed such that the opening of the defect is flush with the uninjured bone surface.

A covering as provided herein may further comprise an attachment or coupling mechanism. Any suitable attachment mechanism can be used, such as a tab, loop, tack or other structure adapted for attachment at the site. Also, for example, a covering may include a hook-and-eye (Velcro™) portion. The hook-and-eye portion may be used to couple the covering to a tissue structure, such as bone, or to another covering. For example, a dual compartment covering may be formed by two single-compartment coverings coupled at complementary ends thereof. For example, the coupling portion may comprise overlapping/mating Velcro™ portions. The size and shapes of the single compartment coverings may be the same or may be different. Further, the materials of the compartment coverings and the substances provided therein may be the same or may be different. The coupling may be done pre-implantation or post-implantation. In post-implantation embodiments, the coupling may be done by inserting first and second coverings through an opening into a space and coupling the coverings within the space. Other suitable attachment, or coupling, mechanisms are described more fully below.

In some embodiments, the covering may be labeled. Such labeling may be done in any suitable manner and at any suitable location on the covering. In some embodiments, labeling may be done by using a silk screen printing, using an altered weaving or knotting pattern, by using different colored threads, or other. The labeling may indicate information regarding the covering. Such information might include part number, donor id number, number, lettering or wording indicating order of use in the procedure or implant size, etc.

Compartments

A covering may comprise a single compartment implant body in any shape or form. In further exemplary embodiments, the covering may be a narrow tube for delivery through a catheter. For example, the covering may be delivered percutaneously using a catheter through which it is inserted. Thus, the covering may have dimensions suitable for receipt in the catheter. Optionally, the covering may be stiffened to facilitate insertion into the catheter. Such stiffening may be achieved through choice of material for the covering, by treating the material of the covering, or other. In some embodiments, the covering may be coated with a material to facilitate sliding engagement with the catheter.

As to volume, advantageous implant bodies can have a total volume of at least about 2 cubic centimeters (cc), e.g. in the range of about 2 cc to about 100 cc, and more typically in the range of about 10 cc to about 50 cc, although both smaller and larger overall volumes may also be used. Similarly, the volume of the pieces into which the implant bodies are configured to be separated may range from about 1 cc to about 50 cc, more typically in the range of about 5 cc to about 20 cc, although other piece volumes will also be suitable in broader aspects of the present principles.

In other examples, the covering of an implant body includes score lines for enabling portions of the body to be separated. The delivery system may be used in its entirety at an implant site or may be manipulated by the user to separate the implant body into multiple smaller pieces, some or all of which may be used, at a single implant site or at multiple different implant sites.

In one embodiment of a single compartment covering, a plurality of substances may be provided within the covering based on characteristics of the substances. For example, where it is desirable to include a particulated first substance within a material having mesh openings larger than the substance, a second substance may be provided surrounding the particulated first substance (e.g., modified demineralized allograft material) to reduce the likelihood of release of particles of the first substance from the mesh. Thus, for example, a particulated first substance and a particulated second substance may be provided wherein the particles of the first substance have a smaller size than the particles of the second substance. A covering is provided comprising a mesh having mesh openings or pores larger than the particles of the first substance. For use, the first substance is provided generally centrally within the covering, the second substance is provided around the first substance and thus between the first substance and the second substance. In further embodiments, the second substance may be coated, for example via spray coating or solvent casting.

In yet a further embodiment, a single compartment covering may be used as a spacer for nonunion. For example, the covering may be placed in a canal of a long bone.

Multi Compartment

In alternative embodiments, the covering may comprise a plurality of compartments. For example, the covering may comprise nested coverings, coverings coupled via a temporary barrier, coverings separated with a boundary, and others, described below. In embodiments comprising two compartments, a second compartment may be adjacent, apart from, inside, or surrounding a first compartment. Materials for the first compartment and the second compartment (which may be designated first and second substances) may be the same, partially the same, or different. The materials for the first compartment and the second compartment may have different release profiles, different porosities, and other different characteristics. Selection of materials, positioning of the compartments, and other factors relating to the first and second compartments may be chosen to achieve simultaneous or sequential delivery or release of a substance or substances. A first substance may be provided in the first compartment and a second substance may be provided in the second compartment. In some embodiments, an osteoinductive substance may be placed in a compartment generally adjacent tissue being treated as implanted and an osteoconductive substance may be placed in a compartment not adjacent tissue being treated. Release rates for the materials provided in the first compartment and the second compartment may be different. In some embodiments, at least one of the compartments may be unfilled at the time of surgery and autograft or other material may be provided therein in the operating room or at the surgical site. In some embodiments, the covering may form a 3D scaffold.

In any of the discussed examples the surgeon may select the number of portions of the body or number of compartments desired for placement and cut or pull/tear along the score lines or perforations providing the desired number of portions or compartments. Further, if the covering is made of a material that is brittle or strain hardens, the surgeon may separate the compartments by bending the selected portion back upon itself and reversing until the segments separate. In some embodiments, every other compartment, for example, may be preloaded or filled with a substance for delivery. Alternatively, only some of the compartments may be preloaded, for example, every other compartment may be preloaded such that alternating compartments may be filled in the operating room or at the surgical site.

In some embodiments, at least one but not all of the compartments may be weight-bearing. In other embodiments, all of the compartments may be weight-bearing.

In one embodiment, the covering may comprise a penetrable material at a first compartment configured for placement adjacent bone and a substantially impenetrable material at a second compartment configured for placement adjacent soft tissue. Alternatively, the material of the compartments may have substantially identical characteristics. The covering then can be positioned in any desirable manner. By way of example only, a covering may have a porous surface that is positioned adjacent bone, and a separate or opposite surface that has a generally impenetrable surface that is positioned adjacent soft tissue. Alternatively, a covering may have one compartment that comprises a porous material, and a second compartment that comprises a substantially impenetrable material.

In another embodiment, the covering may comprise a continuous tube wherein the tube may be twisted to divide portions of the tube. The tube thus may be divided into a series of implants, each having ends that may be twisted or heat treated. Any suitable manner of dividing the tube into a plurality of compartments may be used. For example, the tube may be crimped, heat treated, twisted, knotted, stapled, sewn, or otherwise divided. Any suitable tool may be used for dividing the tube into such compartments including, for example, a crimper, a heat tool, or other.

In some embodiments, a multi-compartment covering may be configured to be foldable and stackable.

For both single and multi-compartment coverings, the covering may be closed after filling substances. Accordingly, the covering may be provided in an unfilled, unsealed state. After a substance for delivery is placed in the covering, the covering may be permanently or temporarily closed. Permanent closure may be, for example, by heat sealing, stitching, adhesion, or other methods. Temporary closure may be by tying, fold lock, cinching, and etc. A temporarily closed covering can be opened without damaging the covering during surgical implantation to add or remove substances in the covering.

Attachment Mechanisms

The covering may be configured with structures to permit attachment at the surgical site, such as to skeletal tissue or to soft tissue structures, or for attachment to other coverings, or for attachment to adjacent implantable medical devices or products (such as a rod or screw or cross-brace of a pedicle screw fixation system, a hip prosthesis, a bone plate, and the like). Generally, the attachment mechanism may be used to retain the covering at the surgical site and any mechanisms capable of doing so may be used. The attachment may be to bone or to adjacent tissues such as muscle, tendon, or ligament. Where the covering retains a bone graft substance, the covering may be held in a relatively stable position relative to bone (or relative to the surgical site or surgical defect) to promote bone growth. Accordingly, in some embodiments, the delivery system may be suitable for assisting in attaching tendons, artificial tendons, or ligaments to bone or other structure.

The bone or soft tissue to which the covering is attached may be prepared for receiving the attachment mechanism(s). For example, in spinal applications, slots or perforations may be provided in posterior elements such as transverse processes, spinous processes, or other bone or tissue to receive the attachment mechanism.

Any suitable attachment mechanism may be used, including mechanical, physical, chemical, and biological attachment mechanisms. The attachment mechanism may be provided at an end of the covering, centrally in or on the covering, generally in or on the body of the covering, or any combinations of these. When an attachment mechanism is used to couple first and second coverings to one another, such attachment or coupling may be done pre-implantation or post-implantation. In post-implantation embodiments, the coupling may be done by inserting first and second coverings through an opening into a space and coupling the coverings within the space. In some embodiments, the covering may be provided with attachment mechanisms to facilitate suturing or other attachment of the covering in vivo.

In some embodiments, a covering may include an area for receipt of an attachment mechanism. For example, a covering may include a tab for receipt of a screw. In other embodiments, an attachment mechanism may interface with any portion of the covering. For example, a screw attachment mechanism may be threaded through a covering at any location, including central to a containment area of the covering. In some embodiments, a screw attachment mechanism may be threaded through the covering and the substance provided in the containment area of the covering.

A further method of attachment may comprise suturing or otherwise attaching the covering to a tether, anchor, or screw embedded in a bony structure, e.g. a pedicle screw of a spinal stabilization system. Such screw, anchor, or tether may pass through the covering and its contained contents to provide fixation, or through a tab at a margin of the covering, or through other structure of the covering.

Chemical attachment mechanisms may comprise, for example, a bioadhesive or glue, cement, tape, tissue adhesives, or similar mechanism. Chemical attachment mechanisms may further comprise mechanisms that facilitate cross-linking. In further embodiments, attachment mechanisms such as crimping, welding, soldering, or brazing may be used. For example, tissue welding may be used. Further, attachment may be achieved via friction.

Suitable adhesives for use may include, for example, cyanoacrylates (such as histoacryl, B Braun, which is n-Butyl-2 Cyanoacrylate; or Dermabond, which is 2-octylcyanoacrylate); epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. Adhesives may be selected for use based on their bonding time; e.g., in some circumstances, a temporary adhesive may be desirable, e.g., for fixation during the surgical procedure and for a limited time thereafter, while in other circumstances a permanent adhesive may be desired. Where the compartment is made of a material that is resorbable, the adhesive can be selected that would adhere for about as long as the material is present in the body. In some embodiments, the covering material may be treated to form chemical linkages between the covering and adjacent tissue, whether bone or soft tissue.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms.

Generally, any combination of mechanical, physical, chemical, or biological attachment mechanisms may be used.

Any of the various attachment mechanisms may be provided as part of the covering or may be supplied separately. In various embodiments, the attachment mechanisms may be integral to the covering. Alternatively, the attachment mechanisms may be secured to the covering, for example, by stitching, welding, crimping, or other. The attachment mechanisms may have any suitable geometric configuration and may optionally include apertures for receiving other components for coupling in vivo, such as an aperture for receiving a screw. Thus, for example, an attachment mechanism may be provided configured for receiving an anchor for fixation to bone. Generally, any number of attachment mechanisms may be provided at any suitable location on the covering.

The attachment mechanisms may be manufactured of the same material as the portion of the covering to which it is coupled or may be manufactured of a different material from the portion of the covering to which it is coupled. The attachment mechanism may be resorbable or nonresorbable. The material of the attachment mechanism may be selected to allow anchoring the covering to an adjacent covering having a complementary attachment mechanism or to another structure. In various embodiments, the attachment mechanism may comprise, allograft, synthetic materials, demineralized bone, nondemineralized bone, other material, or combinations of these. The shape and size of the attachment mechanism may be selected based on application.

In some embodiments, the covering may be tubular and have threaded ends such that the ends may be threaded with a reciprocal thread of a further device or implant. For example, the covering may be used with interference screws. In some embodiments, the covering may include extensions or tabs that may be used for wrapping around or suturing to the surgical site. Alternatively, the covering may be sutured directly to the surgical site. The ends of the covering may be presealed or may be sealed after introduction of contents. Sealing may be done by using adhesives, heating, solvent treatment, suturing, knotting, or any other means.

Substance for Delivery by Covering

A substance may be provided in the covering, before or during surgery (as described herein), for delivery in vivo. Generally, the substance or material may be homogenous or heterogeneous. The substance or material may be selected to exhibit certain gradients. For example, the substance or material may be selected to exhibit a gradient to guide, lure, or attract cells along a pathway. Such gradient may comprise a cell gradient, a cell type gradient (for example transitioning from bone cells to cartilage cells or transitioning from bone cells to tendon cells), a gradient of conductivity, or a gradient of density/porosity.

The covering may be used to deliver a substance comprising any suitable biocompatible material. In some embodiments, the substance may comprise a biocompatible material comprising a demineralized allograft bone material modified to provide an ionic gradient to produce a modified demineralized allograft bone material as per some embodiments of the present disclosure, which, when implanted, results in enhanced ingrowth of host bone. Namely, a demineralized allograft bone material may be modified in such a way that the original chemical forces naturally present have been altered in such a way as to attract and bind growth factors, other proteins and cells affecting osteogenesis, osteoconduction and osteoinduction.

In some embodiments, the demineralized allograft bone material comprises demineralized bone matrix fibers and demineralized bone matrix chips in a 30:60 ratio.

In some embodiments, the substance or material may comprise a sequence of ingredients.

In specific embodiments, the covering may be used to deliver surface demineralized bone chips, optionally of a predetermined particle size, demineralized bone fibers, optionally pressed, and/or allograft. For embodiments wherein the substance is biologic, the substance may be autogenic, allogenic, xenogenic, or transgenic. Other suitable materials that may be positioned in the covering include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In some embodiments, the substance may be pressed before placement in the covering. A substance provided within the covering may be homogenous, or generally a single substance, or may be heterogeneous, or a mixture of substances.

In some embodiments, the substance may be designed to expand in vivo. Such an embodiment may be used to fill a space and create contact with congruent surfaces as it expands in vivo, for example for interbody fusion. Thus, in some embodiments, the delivery system may be used in the disc space, between implants, or inside a cage.

The covering retains the substance in place by pressure against the covering. The covering thus may, in some embodiments, maintain particles of substance in close proximity (for example, where the covering retains a substance comprising bone particles). Generally, the ratio of covering material to substance for placement within the covering may be low. For example, in some embodiments, the ratio of covering material to substance, by weight, may be approximately 1:1,000, 1:100, 1:50, 1:25, 1:1, or any suitable ratio that may be higher or lower than these.

In some embodiments the substance delivered by the covering may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anticholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-β); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In one embodiment of a covering comprising two compartments, a first growth factor may be provided for delivery by the first compartment and a second growth factor may be provided for delivery by the second compartment. The first and second growth factors may be provided with other substances. The first and second growth factors may be selected (and placed in respective compartment for positioning in vivo) based on desired characteristics of the growth factor. For example, an angiogenic growth factor may be provided in the first compartment and an osteoinductive growth factor may be provided in the second compartment.

Similarly, the substance delivered by the first compartment and the substance delivered by the second compartment may be selected based on desired characteristics of the compartment according to its placement in vivo. Thus, for example, one compartment may have a substance that is substantially osteoclast stimulating while another compartment may have a substance that is substantially osteoblast stimulating.

In one embodiment, demineralized bone fibers may be provided in the first compartment and surface demineralized bone chips may be provided in the second compartment. In this embodiment, the demineralized bone fibers may generally provide osteoinductive characteristics and the surface demineralized chips may generally provide osteoinductive and/or osteoconductive characteristics. In use, the covering may be laid flat on the transverse process and positioned such that the first compartment, holding the demineralized bone fibers, is nearest the vertebral body and the second compartment, holding the surface demineralized bone chips, is farther from the vertebral body, or the compartments may be positioned in any other desired configuration. In another embodiment, a covering may comprise first and second compartments wherein autograft may be placed in one of the compartments prior to placement of the covering in vivo, described more fully below. In other embodiments, three or more compartments may be used, as appropriate for the materials being delivered and the application of the compartmented implant. More than one substance may be provided in a compartment. For example, surface demineralized bone chips and demineralized bone fibers may be mixed and provided within a single compartment. Such mixture of substances within a single compartment may be a substantially uniform mix or may be a plurality of substances placed in the compartment separately such that they are substantially unmixed. When multiple compartments are used, each compartment may contain one or more substances. Exemplary substances that may be provided in one or more compartments of the delivery system include cells from the osteogenic precursors, growth factors, angiogenic factors and other active proteins including bone morphogenic proteins, and cellular scaffolding materials of natural or synthetic origin, antibiotics, and other substances described below.

In some embodiments, other medical devices may be provided within the covering. For example, one or more electrical stimulator electrodes may be provided within the covering.

Sterilization

The medical device including the covering and/or its contents may be sterilizable. In various embodiments, one or more components of the covering and/or its contents are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device and/or covering. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device and/or covering. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the medical device and/or covering is included in a gel.

Other methods may also be used to sterilize the device and/or covering and/or one or more components of the device and/or covering, including, but not limited to, gas sterilization, such as, for example, with ethylene oxide or steam sterilization.

Method of Use

The covering delivers the substance or substances in vivo. Such delivery may be active, passive, by diffusion, or other. Active delivery may include the degradation or decomposition of the covering with the interaction of body fluids, extracellular matrix molecules, enzymes or cells. It may also include the cleavage of physical and/or chemical interactions of substance from covering with the presence of body fluids, extracellular matrix molecules, enzymes or cells. Further, it may comprise formation change of substances (growth factors, proteins, polypeptides) by body fluids, extracellular matrix molecules, enzymes or cells.

The covering is loaded with the substance for placement in vivo. The covering may be pre-loaded, thus loaded at manufacture, or may be loaded in the operating room or at the surgical site. Preloading may be done with any of the substances previously discussed including, for example, DBM, synthetic calcium phosphates, synthetic calcium sulfates, enhanced DBM, collagen, carrier for stem cells, and expanded cells (stem cells or transgenic cells). Loading in the operating room or at the surgical site may be done with any of these materials and further with autograft and/or bone marrow aspirate.

Any suitable method may be used for loading a substance in the covering in the operating room or at the surgical site. For example, the substance may be spooned into the covering, the substance may be placed in the covering using forceps, the substance may be loaded into the covering using a syringe (with or without a needle), or the substance may be inserted into the covering in any other suitable manner. Specific embodiments for loading at the surgical site include for vertebroplasty or for interbody space filler.

For placement, the substance or substances may be provided in the covering and the covering placed in vivo. In one embodiment, the covering is placed in vivo by placing the covering in a catheter or tubular inserter and delivering the covering with the catheter or tubular inserter. The covering, with a substance provided therein, may be steerable such that it can be used with flexible introducer instruments for, for example, minimally invasive spinal procedures. For example, the osteoimplant may be introduced down a tubular retractor or scope, during XLIF, TLIF, or other procedures. In other embodiments, the covering (with or without substance loaded) may be placed in a cage, for example for interbody fusion.

In continuous tube embodiments, the surgeon may divide the tube into the desired number of compartments, using a crimper, heat tool or other. Alternatively, in an embodiment wherein the tube is perforated into a plurality of compartments, the surgeon may select the number of compartments desired and cut along the applicable perforation. In some embodiments, some of the compartments may be prefilled with a substance for delivery and other compartments may be empty for filling by the surgeon. For example, ever other compartment between perforations may be preloaded or filled. The osteoimplant thus may be customized by filling the empty compartments with a desired substance.

For example, in some embodiments, a portion of the covering for example, one compartment of a multi-compartment covering, may be filled with autograft. Thus, the covering may be substantially empty prior to surgery. During surgery, a surgeon may remove autograft from the patient and place the autograft in the substantially empty compartment. Such placement may be done in any suitable manner. In one embodiment, the covering may be provided with a port for receiving an opening of an injection device and the autograft may be injected into the covering. Alternatively, the autograft may be mixed with allograft, synthetics, or any other desired substances or combination of substances.

Attachment mechanisms provided on the covering may be used to couple the covering to a site in vivo.

Applications

The covering may be used in any suitable application. In some embodiments, the covering may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The delivery system may be used in a minimally invasive procedure via placement through a small incision, via delivery through a tube, or other. The size and shape may be designed with restrictions on delivery conditions.

An exemplary application for using a delivery system as disclosed is fusion of the spine. In clinical use, the covering and delivered substance may be used to bridge the gap between the transverse processes of adjacent or sequential vertebral bodies. The delivery system may be used to bridge two or more spinal motion segments. The covering surrounds the substance to be implanted, and contains the substance to provide a focus for healing activity in the body.

In other applications, the delivery system may be applied to transverse processes or spinous processes of vertebrae.

Generally, the delivery system may be applied to a pre-existing defect, to a created channel, or to a modified defect. Thus, for example, a channel may be formed in a bone, or a pre-existing defect may be cut to form a channel, for receipt of the delivery system. The covering may be configured to match the channel or defect. In some embodiments, the configuration of the covering may be chosen to match the channel. In other embodiments, the channel may be created, or the defect expanded or altered, to reflect a configuration of the covering. The covering may be placed in the defect or channel and, optionally, coupled using attachment mechanisms.

At the time just prior to when the delivery system is to be placed in a defect site, optional materials, e.g., autograft bone marrow aspirate, autograft bone, preparations of selected autograft cells, autograft cells containing genes encoding bone promoting action, etc., can be combined with the covering and/or with a substance provided within the covering. The osteoimplant can be implanted at the bone repair site, if desired, using any suitable affixation means, e.g., sutures, staples, bioadhesives, screws, pins, rivets, other fasteners and the like or it may be retained in place by the closing of the soft tissues around it.

In accordance with various embodiments, a delivery system for delivery of a substance in vivo is provided. The delivery system comprises a covering and a substance. The covering may be a single or multi-compartment structure capable of at least partially retaining a substance provided therein until the covering is placed at a surgical site. The covering may include separation-assist lines such as perforations or score lines. Upon placement, the substance may be released (actively or passively) to the surgical site. The covering may participate in, control, or otherwise adjust, the release of the substance. The delivery system may be used to control availability of a substances provided within the delivery system to cells and tissues of a surgical site over time.

Although the disclosure has been described with reference to some embodiments, persons skilled in the art will recognize that changes may be made in form and detail without departing from the spirit and scope of the disclosure.

What is claimed is:

1. A method for enhancing ingrowth of host bone comprising: modifying at least a portion of a demineralized allograft bone material comprising fully demineralized bone matrix fibers and surface demineralized bone matrix chips at a ratio of about 30:60 to provide an ionic gradient to produce a modified demineralized allograft bone material; applying pressure to the fully demineralized bone matrix fibers and surface demineralized bone matrix chips to press them together; disposing a porous polymeric mesh multi-compartment covering configured to be foldable and stackable comprising PGA or PLA, clonidine and a plasticizer comprising mPEG with the demineralized allograft bone material; treating the mesh to increase solubility; coating the porous polymeric mesh multi-compartment covering with D,L-lactide having a thickness of about 25 to 50 microns to modify release of the clonidine; and implanting the modified demineralized allograft bone material, wherein the modifying comprises application of an enzyme comprising cathepsin L, cathepsin K, cathepsin B, plasminogen, plasminogen activators, elastase or stromelysin to the demineralized allograft bone material.

2. A method of claim 1, further comprising contacting the modified demineralized allograft bone material with a cell culture, or a combination thereof.

3. A method of claim 2, wherein the cell culture comprises at least one of mesenchymal stem cells, periosteal cells, pluripotent stem cells, osteoprogenitor cells, osteoblasts, osteoclasts, bone marrow-derived cell lines, or a combination thereof.

4. A method of claim 1, wherein the demineralized allograft bone material comprises a composite bone.

5. A method of claim 4, wherein the composite bone comprises a bone powder in an amount from about 20% to about 60% w/w, a polymer in an amount from 20% to about 60% w/w and demineralized bone particles in an amount from about 20% to about 40% w/w.

6. A method of claim 1, wherein the modifying further comprises a one-to-one substitution of the calcium ion in calcium hydroxyapatite with an element comprising at least one of a lithium ion, sodium ion, potassium ion and cesium ion.

7. A method of claim 1, wherein the step of applying pressure is performed after the step of providing an ionic gradient, and further comprises deactivating the enzyme after the step of applying pressure.

8. A method of claim 1, wherein the step of treating the mesh to increase solubility comprises applying supercritical carbon dioxide, supercritical nitrogen, or supercritical water to the mesh.

9. A method of claim 1, wherein the step of treating the mesh to increase solubility comprises applying explosive decompression to the mesh.

\* \* \* \* \*